US012663430B2

(12) United States Patent
Gao et al.

(10) Patent No.: US 12,663,430 B2
(45) Date of Patent: Jun. 23, 2026

(54) AUTOMATED LIBRARY PREPARATION SYSTEM

(71) Applicant: MGI Tech Co., Ltd., Shenzhen (CN)

(72) Inventors: Jiandong Gao, Shenzhen (CN); Jing Li, Shenzhen (CN); Zhongxun Luo, Shenzhen (CN); Liangying Zou, Shenzhen (CN)

(73) Assignee: MGI Tech Co., Ltd., Shenzhen (CN)

( * ) Notice: Subject to any disclaimer, the term of this patent is extended or adjusted under 35 U.S.C. 154(b) by 678 days.

(21) Appl. No.: 18/016,261

(22) PCT Filed: Jul. 15, 2020

(86) PCT No.: PCT/CN2020/102150
§ 371 (c)(1),
(2) Date: Jan. 13, 2023

(87) PCT Pub. No.: WO2022/011604
PCT Pub. Date: Jan. 20, 2022

(65) Prior Publication Data
US 2023/0280361 A1 Sep. 7, 2023

(51) Int. Cl.
*G01N 35/00* (2006.01)
*B01L 3/00* (2006.01)
(Continued)

(52) U.S. Cl.
CPC .... *G01N 35/0099* (2013.01); *B01L 3/502761* (2013.01); *B01L 7/52* (2013.01);
(Continued)

(58) Field of Classification Search
None
See application file for complete search history.

(56) References Cited

U.S. PATENT DOCUMENTS 5,158,895 A * 10/1992 Ashihara .......... G01N 33/54326
435/7.1
5,240,678 A * 8/1993 Litsche .................. G01N 35/04
422/65
(Continued)

FOREIGN PATENT DOCUMENTS

CN 106285355 A 1/2017
CN 206096158 U 4/2017
(Continued)

*Primary Examiner* — Brian R Gordon
(74) *Attorney, Agent, or Firm* — ScienBiziP, P.C.

(57) ABSTRACT

An automated library preparation system (1) includes a consumable item storage module (10) for storing a consumable item; a dispatching transfer module (30) capable of moving along a predetermined direction; a biochemical reaction module (20) including a plurality of biochemical reaction devices (21a, 21b) which are arranged in turn along the predetermined direction, each of the plurality of biochemical reaction devices being configured to perform one subprocess of sample preparation for gene sequencing, the dispatching transfer module (30) being configured to grab the consumable item (2) stored in the consumable item storage module, the dispatching transfer module being further configured to transfer the consumable item to the plurality of biochemical reaction devices when sliding along the predetermined direction; and a control module configured to control the consumable item storage module, the biochemical reaction module, and the dispatching transfer module to work collaboratively.

9 Claims, 16 Drawing Sheets

(51) Int. Cl.
  *B01L 7/00* (2006.01)
  *C12Q 1/6869* (2018.01)
  *G06Q 10/087* (2023.01)

(52) U.S. Cl.
  CPC ..... *C12Q 1/6869* (2013.01); *G01N 35/00584* (2013.01); *G06Q 10/087* (2013.01); *B01L 2200/0668* (2013.01); *B01L 2300/18* (2013.01); *G01N 2035/00495* (2013.01)

(56) References Cited

U.S. PATENT DOCUMENTS

| | | | | |
|---|---|---|---|---|
| 5,275,951 A * | 1/1994 | Chow | ............... | G01N 35/0098 |
| | | | | 422/930 |
| 5,518,688 A * | 5/1996 | Gianino | .......... | G01N 35/00029 |
| | | | | 422/561 |
| 5,928,952 A | 7/1999 | Hutchins et al. | | |
| 5,985,214 A * | 11/1999 | Stylli | ................ | G01N 35/1002 |
| | | | | 700/214 |
| 6,669,432 B2 * | 12/2003 | Hamel | ................... | G01N 35/10 |
| | | | | 422/511 |
| 6,673,316 B1 * | 1/2004 | Okamoto | ............. | B01J 19/0046 |
| | | | | 422/65 |
| 6,919,044 B1 * | 7/2005 | Shibata | .............. | G01N 35/0092 |
| | | | | 422/65 |

| | | | | |
|---|---|---|---|---|
| 2002/0009394 A1 | 1/2002 | Koster et al. | | |
| 2003/0044321 A1 * | 3/2003 | Haslam | .................. | G01N 35/04 |
| | | | | 422/65 |
| 2003/0215360 A1 * | 11/2003 | Ruddock | .............. | G01N 35/109 |
| | | | | 422/65 |
| 2003/0223916 A1 * | 12/2003 | Testrut | ...................... | B01L 9/06 |
| | | | | 422/63 |
| 2006/0216207 A1 * | 9/2006 | Lehto | ................... | G01N 35/109 |
| | | | | 422/510 |
| 2008/0063562 A1 * | 3/2008 | Hoover | .................. | B25J 15/026 |
| | | | | 422/63 |
| 2008/0090288 A1 * | 4/2008 | Hibino | ................... | C12M 37/00 |
| | | | | 435/283.1 |
| 2009/0142844 A1 * | 6/2009 | Le Comte | ......... | G01N 35/0099 |
| | | | | 901/6 |
| 2016/0238627 A1 * | 8/2016 | Raicu | ................... | G01N 35/026 |
| 2017/0219614 A1 * | 8/2017 | Cook | ................. | G01N 35/1065 |
| 2020/0109015 A1 * | 4/2020 | Newberg | .............. | B25J 9/0093 |
| 2020/0141961 A1 | 5/2020 | Ahlfors | | |

FOREIGN PATENT DOCUMENTS

| | | | |
|---|---|---|---|
| CN | 107345199 A | 11/2017 |
| CN | 207243909 U | 4/2018 |
| CN | 108333112 A | 7/2018 |
| CN | 110628608 A | 12/2019 |

* cited by examiner

11a(11b)

111

113

112

110

111

1110

1111

1113

1112

11a(11b)

110

113

21a(21b)

214
218
212
211
215
213
210

212

21a(21b)

217

50

51

60

61

81a(81b)

815

813

811

2

812

810

814

812

8123

8122

8124

8121

AUTOMATED LIBRARY PREPARATION SYSTEM

FIELD

The subject matter relates to automated sample preparation for gene sequencing, and more particularly, to an automated library preparation system.

BACKGROUND

At present, there is no solution with high automation degree for sample preparation before the next-generation sequencing. Generally, a plurality of independent instruments are required to complete the entire process of sample preparation. With the development of gene sequencing industry, gene sequencing technology has gradually been widely used in clinical experiments. Therefore, an integrated automated library preparation system is urgently needed to prepare front-end samples.

SUMMARY

The present disclosure provides an automated library preparation system, the automated library preparation includes:

a consumable item storage module configured for storing a consumable item;

a dispatching transfer module movable along a predetermined direction;

a biochemical reaction module including a plurality of biochemical reaction devices which are arranged in turn along the predetermined direction, each of the plurality of biochemical reaction devices being configured to perform one subprocess of sample preparation for gene sequencing, the dispatching transfer module being is configured to grab the consumable item stored in the consumable item storage module, the dispatching transfer module being further configured to transfer the consumable item to the plurality of biochemical reaction devices as the dispatching transfer module sliding along the predetermined direction; and a control module configured to control the consumable item storage module, the biochemical reaction module, and the dispatching transfer module to work collaboratively.

In some embodiments of the present disclosure, the automated library preparation system is divided into at least two processing areas which are separated from each other, the plurality of the biochemical reaction devices are respectively located in the at least two processing areas.

In some embodiments of the present disclosure, a transfer window device is arranged between two adjacent processing areas, the transfer window is configured to maintain separation between the two adjacent processing areas when the dispatching transfer module transfers the consumable item from a previous processing area to a current processing area.

In some embodiments of the present disclosure, the transfer window device includes a separating block, a front automatic door, and a rear automatic door, the front automatic door and the rear automatic door are disposed on the separating block and opposite to each other, the separating block defines a consumable item accommodation chamber, the consumable item accommodation chamber is configured to accommodate the consumable item transferred from the previous processing area, the front automatic door and the rear automatic door are configured to close opposite sides of the consumable item accommodation chamber when the front automatic door and the rear automatic door are closed, when one of the front automatic door and the rear automatic door is opened, the other is closed.

In some embodiments of the present disclosure, the consumable item storage module includes a plurality of consumable item storage devices, the plurality of consumable item storage devices are respectively located in the at least two processing areas, the consumable item storage device is configured to provide the consumable item for biochemical reaction devices in the same processing area.

In some embodiments of the present disclosure, each of the plurality of consumable item storage devices includes:

a storage rack for storing the consumable item;

a discharging support plate; and a discharging manipulator configured for clamping the consumable item in the storage rack and transfer clamped consumable item to the discharging support plate, wherein the dispatching transfer module is configured to grab the consumable item on the discharging support plate.

In some embodiments of the present disclosure, the consumable item storage devices in at least one processing area includes a normal temperature type consumable item storage device and a low-temperature type consumable item storage device, the normal temperature type consumable item storage device is configured to provide a room temperature storage environment for storing the consumable item, the low-temperature type consumable item storage device is configured to provide a low-temperature storage environment for storing the consumable item.

In some embodiments of the present disclosure, the dispatching transfer module includes dispatching transfer devices disposed in each of the at least two processing areas, each dispatching transfer device includes a slide rail extending in the predetermined direction and a dispatching transfer assembly slidably arranged on the slide rail, the dispatching transfer assembly includes a dispatching manipulator and a clamping jaw connected to the dispatching manipulator, the dispatching manipulator is configured to adjust a position of the clamping jaw to cause the clamping jaw to align with the consumable item storage devices and the biochemical reaction devices.

In some embodiments of the present disclosure, the automated library preparation system further includes a film sealing device and a film peeling device, the film sealing device being configured to apply a packaging film on the consumable item, the film peeling device being configured to remove the packaging film on the consumable item.

In some embodiments of the present disclosure, the automated library preparation system further includes a centrifuge device, the centrifuge device being configured to centrifugally process liquid in the consumable item.

The present disclosure realizes the one-stop automated sample preparation process. After the sample is input, the library sample for gene sequencing can be output, human intervention is reduced, and each module can conduct parallel pipeline operations, the throughput and efficiency of library construction are improved. The whole process is carried out in a sealed chamber, environmental pollution and cross-contamination between samples are avoided, the quality of gene sequencing samples is improved, and the results are more accurate and reliable.

BRIEF DESCRIPTION OF THE DRAWINGS

Implementations of the present technology will now be described, by way of embodiment, with reference to the attached figures. Obviously, the drawings are only some embodiments of the present disclosure. For those of ordinary skill in the art, other drawings can be obtained based on these drawings without creative work.

Figure 1:
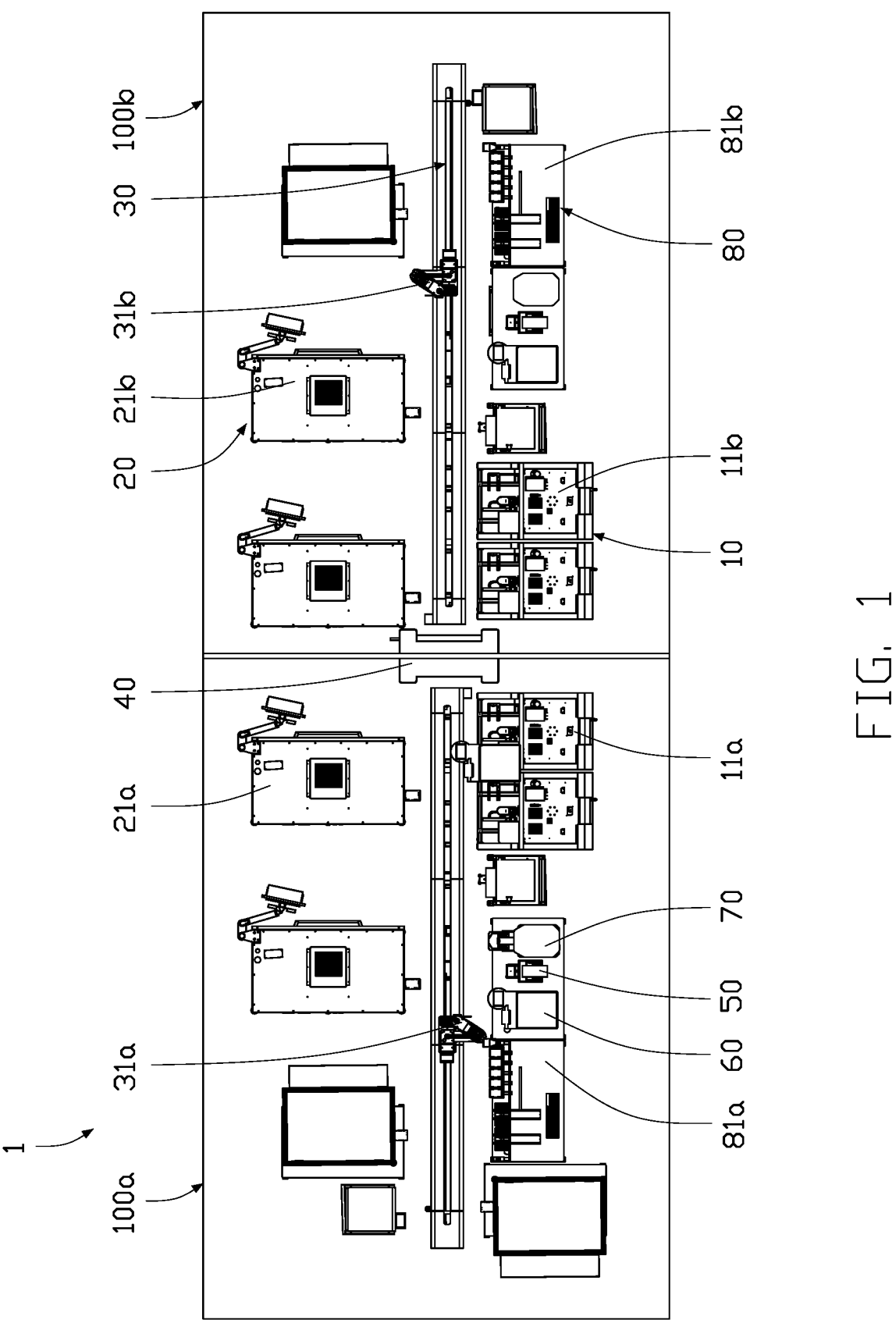
FIG. 1 is a top view of an automated library preparation system according to an embodiment of the present disclosure.

Implementations of the disclosure will now be described, by way of embodiments only, with reference to the drawings.

SYMBOL DESCRIPTION OF MAIN COMPONENTS

Automated library preparation system 1; amplification unit 214; consumable item 2; magnetic bead purification unit 215; consumable item storage module 10; laminar flow hood 216; front consumable item storage device 11a; microplate reader 217; rear consumable item storage device 11b; vibrating unit 218; biochemical reaction module 20; slide rail 311; front biochemical reaction device 21a; dispatching transfer assembly 312; rear biochemical reaction device 21b; consumable item accommodation chamber 410; dispatching transfer module 30; supporting platform 810; front dispatching transfer device 31a; rubber pad stack bit 812; rear dispatching transfer device 31b; third code scanner 813; transfer window device 40; consumable item conveying unit 814; separating block 41; display device 815; front automatic door 42; stock bin 1110; rear automatic door 43; material rack 1111; film sealing device 50; rotating plate 1112; film peeling device 60; support shaft 1113; centrifuge device 70; first code scanner 1120; human-machine interface module 80; horizontal guide rail 1121; front human-machine interface device 81a; vertical guide rail 1122; rear human-machine interface device 81b; pipetting manipulator 2123; pre-processing area 100a; automatic pipette 2124; post-processing area 100b; second code scanner 2125; housing 110; dispatching manipulator 3121; storage rack 111; consumable item buffer plate 3122; discharging manipulator 112; clamping jaw 3123; discharging support plate 113; rubber pad support 8121; frame 210; rubber pad positioning plate 8122; output and input bit 211, 51, 61, 71, 811; silicone pad 8123; pipetting unit 212; handle 8124; temperature control unit 213.

DETAILED DESCRIPTION

Implementations of the disclosure will now be described, by way of embodiments only, with reference to the drawings. The described embodiments are only some embodiments of the present disclosure, rather than all the embodiments. The disclosure is illustrative only, and changes may be made in the detail within the principles of the present disclosure. It will, thus, be appreciated that the embodiments may be modified within the scope of the claims.

It should be noted that when a component is referred to as being "fixed to" or "mounted on" another component, the component can be directly on another component or a middle component may exist therebetween. When a component is considered to be "arranged on" another component, the component can be directly on another component or a middle component may exist therebetween. The term "and/or" as used herein means any combinations of one or more related listed items.

FIG. 1 is a schematic diagram of an entire mechanism of an automated library preparation system according to an embodiment of the present disclosure. The automated library preparation system 1 is used in sample preparation for gene sequencing. The automated library preparation system 1 includes a consumable item storage module 10, a biochemical reaction module 20, a dispatching transfer module 30, and a control module (not shown).

Figure 16:
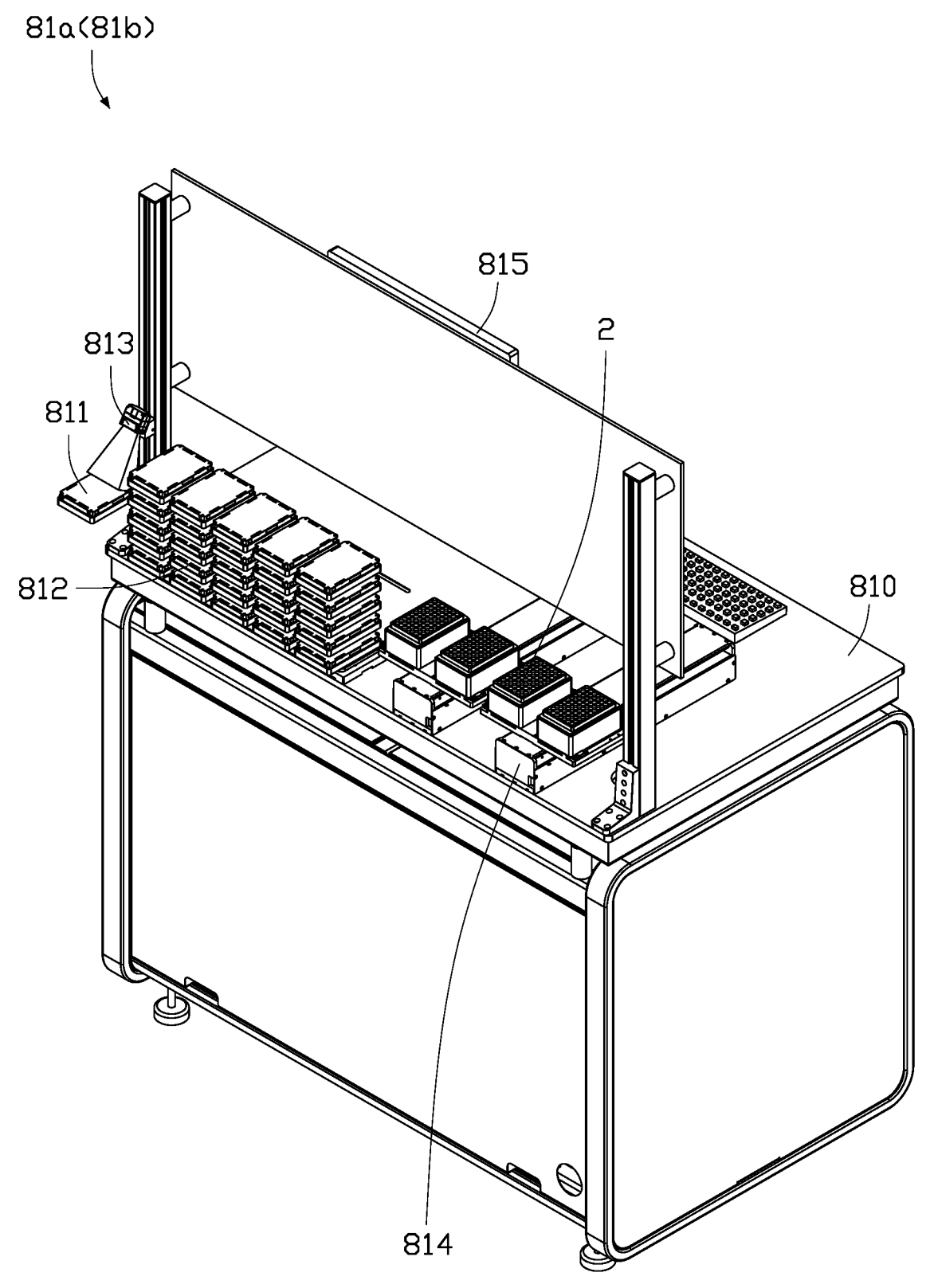
FIG. 16 is a perspective view of a human-machine interface module of the automated library preparation system of FIG. 1.

The consumable item storage module 10 is configured to store consumable items 2 (shown in FIG. 16). The consumable items 2 can be configured to carry biological samples (such as plasma, tissue samples, or cell cultures), as well as various reagents required for the sample preparation for gene sequencing. The consumable items 2 can be, but are not limited to, microporous plates. The dispatching transfer module 30 can move in a predetermined direction. The biochemical reaction module 20 includes a plurality of biochemical reaction devices sequentially arranged along the predetermined direction. The whole process of sample preparation for gene sequencing is divided into different subprocesses, and each biochemical reaction device is configured to execute one of the subprocesses. For example, the plurality of biochemical reaction devices are configured to execute different subprocesses, that is, the biochemical reaction devices have one-to-one correspondence with the subprocesses, or a certain biochemical reaction device can be arranged to correspond to at least two subprocesses, or a certain subprocess can also be arranged to correspond to at least two biochemical reaction devices. The dispatching transfer module 30 is configured to grab the consumable items 2 stored in the consumable item storage module 10, and to transfer the grabbed consumable items 2 to the plurality of biochemical reaction devices as the dispatching transfer module 30 sliding along the predetermined direction, so that the plurality of biochemical reaction devices successively complete corresponding biochemical reaction subprocesses, thereby completing automated sample preparation for gene sequencing. The control module is configured to control the consumable item storage module 10, the biochemical reaction module 20, and the dispatching transfer module 30 to work collaboratively.

For plasma samples, before gene sequencing, it is necessary to perform cell-free nucleic acid extraction, end repair, ligating molecular tag adaptors, purification, amplification by polymerase chain reaction (PCR), purification, quantification and homogenization, and rapid cyclization after library mixing and then to perform rolling circle replication to obtain DNA nanoball (DNB), followed by quantification, and finally obtain the library for gene sequencing. The sequencing library is used as a gene sequencing sample for sequencing by a sequencer. Therefore, as shown in FIG. 1, in this embodiment, the plurality of biochemical reaction devices are respectively configured to perform the subprocesses of cell-free nucleic acid extraction, end repair, ligating molecular tag adaptors, purification, PCR amplification, purification, rapid cyclization after library mixing, DNA nanoball preparation, and quantification and homogenization.

Figure 2:
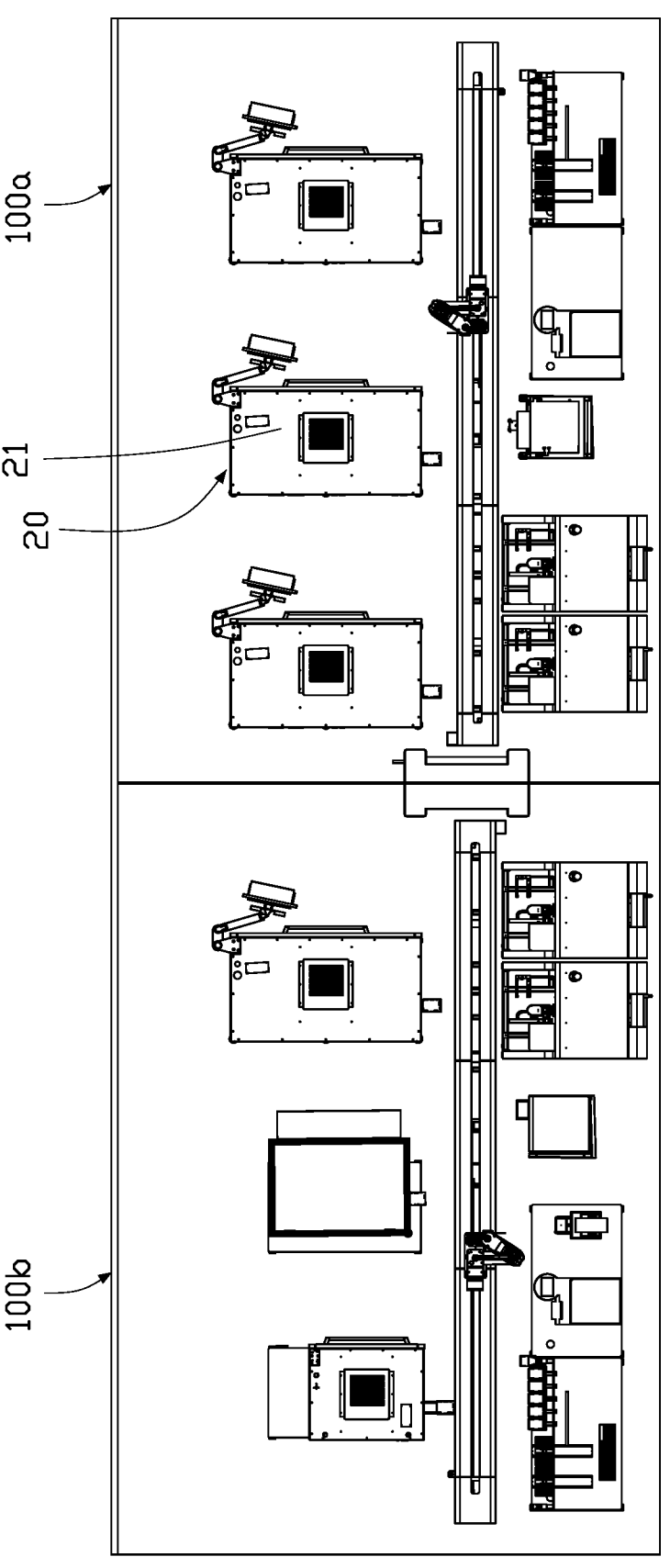
FIG. 2 is a top view of an automated library preparation system according to another embodiment of the present disclosure.

According to different types of samples, the preparation process of the above gene sequencing samples can also be changed. For example, if the sample is cell-free nucleic acid, the subprocess of cell-free nucleic acid extraction is not required, that is, end repair is directly carried out. As shown in FIG. 2, in another embodiment, the plurality of biochemical reaction devices are respectively configured to perform the subprocesses of end repair, ligating molecular tag adaptors, purification, PCR amplification, purification, rapid cyclization after library mixing, DNA nanoball preparation, quantification and homogenization.

As shown in FIG. 1 and FIG. 2, in this embodiment, the automated library preparation system 1 includes at least two processing areas. Each of the two processing areas encloses a closed chamber and the two processing areas are separated from each other. In this embodiment, a case where the automated library preparation system 1 includes a pre-processing area 100a and a post-processing area 100b is taken as an example. The plurality of biochemical reaction devices are respectively located in the pre-processing area 100a and the post-processing area 100b. The specific locations of the pre-processing area 100a and the post-processing area 100b in the automated library preparation system are not limited, and can be set according to actual situation. For the convenience of description, the biochemical reaction device located in the pre-processing area 100a is defined as a front biochemical reaction device 21a, and the biochemical reaction device located in the post-processing area 100b is defined as a rear biochemical reaction device 21b. Furthermore, a transfer window device 40 is arranged between the pre-processing area 100a and the post-processing area 100b. The transfer window device 40 is configured to maintain the separation between the pre-processing area 100a and the post-processing area 100b when the dispatching transfer module 30 transfers consumable items from the pre-processing area 100a to the post-processing area 100b. The transfer window device 40 can be disposed in front of the biological reaction device for PCR amplification, that is, each subprocess before PCR amplification is carried out in the pre-processing area 100a, and each subprocess after PCR amplification and PCR amplification is carried out in the post-processing area 100b, so as to ensure that there is no cross-contamination before and after PCR amplification. It can be understood that in other embodiments, the automated library preparation system 1 can also include three or more processing areas separated from each other.

Figure 3:
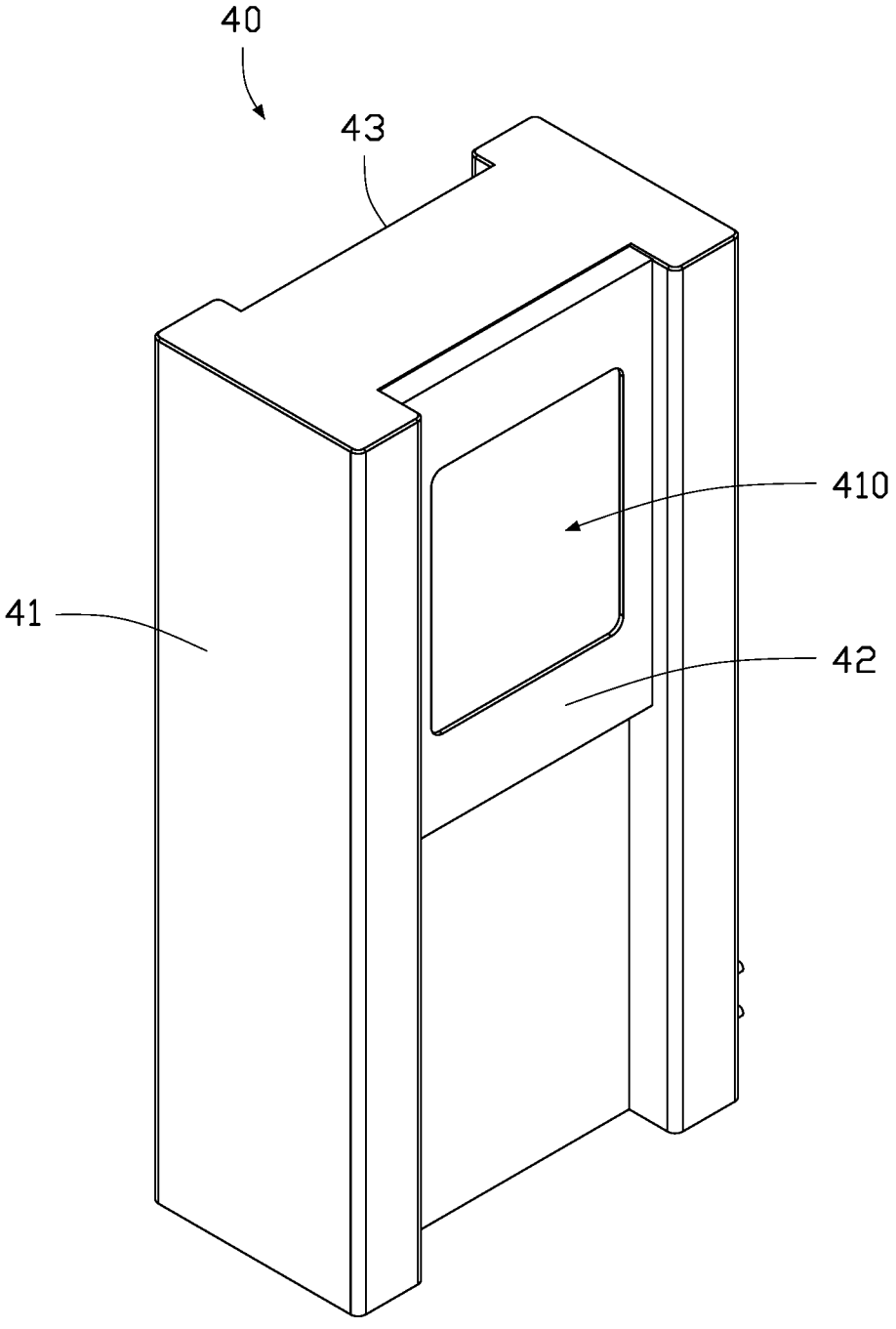
FIG. 3 is a perspective view of a transfer window device of the automated library preparation system of FIG. 1.

Referring to FIG. 3, the transfer window device 40 includes a separating block 41, a front automatic door 42, and rear automatic door 43, the front automatic door 42 and the rear automatic door 43 are disposed on the separating block 41 and opposite to each other. The separating block 41 defines a consumable item accommodation chamber 410, which is configured to accommodate the consumable items 2 transferred from the pre-processing area 100a. The front automatic door 42 and the rear automatic door 43 are configured to close opposite sides of the consumable item accommodation chamber 410 when they are closed. The front automatic door 42 and the rear automatic door 43 cannot be opened at the same time (that is, when one of the front automatic door 42 and the rear automatic door 43 is opened, the other is closed), so as to prevent cross-contamination caused by airflow between the pre-processing area 100a and the post-processing area 100b. When the consumable items 2 are transferred from the pre-processing area 100a to the post-processing area 100b, the front automatic door 42 opens, so that the consumable items 2 are placed in the consumable item accommodation chamber 410, and the rear automatic door 43 remains closed at this time. Specifically, door detection sensors (not shown) are arranged near the front automatic door 42 and the rear automatic door 43 to detect whether the front automatic door 42 or the rear automatic door 43 is open or closed. When the door detection sensors detect that the front automatic door 42 is open, it notifies the rear automatic door 43 to remain closed. Further, a consumable item detection sensor is disposed in the consumable item accommodation chamber 410 to detect whether consumable items 2 is placed in the consumable item accommodation chamber 410. When the consumable item detection sensor detects that the consumable items 2 are placed in the consumable item accommodation chamber 410, the rear automatic door 43 opens. When the door detection sensor detects that the rear automatic door 43 is open, it notifies the front automatic door 42 to close. At this time, the consumable items 2 placed in the consumable item accommodation chamber 410 is removed and consumable item transmission task is completed.

Furthermore, an ultraviolet sterilization lamp (not shown) can be disposed in the consumable item accommodation chamber 410, the ultraviolet sterilization lamp is configured for perform ultraviolet sterilizing on the interior of the consumable item accommodation chamber 410.

As shown in FIG. 1, in this embodiment, the consumable item storage module 10 includes a plurality of consumable item storage devices, which are respectively located in the pre-processing area 100a and the post-processing area 100b to provide consumable items for the biochemical reaction devices in the same processing area 100. For the convenience of description, the consumable item storage device located in the pre-processing area 100a is defined as a front consumable item storage device 11a, and the consumable storage device located in the post-processing area 100b is defined as a rear consumable item storage device 11b. Because different consumable items are often used to carry different samples and reagents in actual use, the front consumable item storage device 11a can be divided into two normal temperature type consumable item storage devices and one low-temperature type consumable item storage device according to the difference in storage temperature or environment of samples and reagents. The normal temperature type consumable item storage device provides a room temperature storage environment for storing the consumable items 2. The low-temperature type consumable item storage device provides a low-temperature storage environment for storing the consumable items 2.

Figure 4:
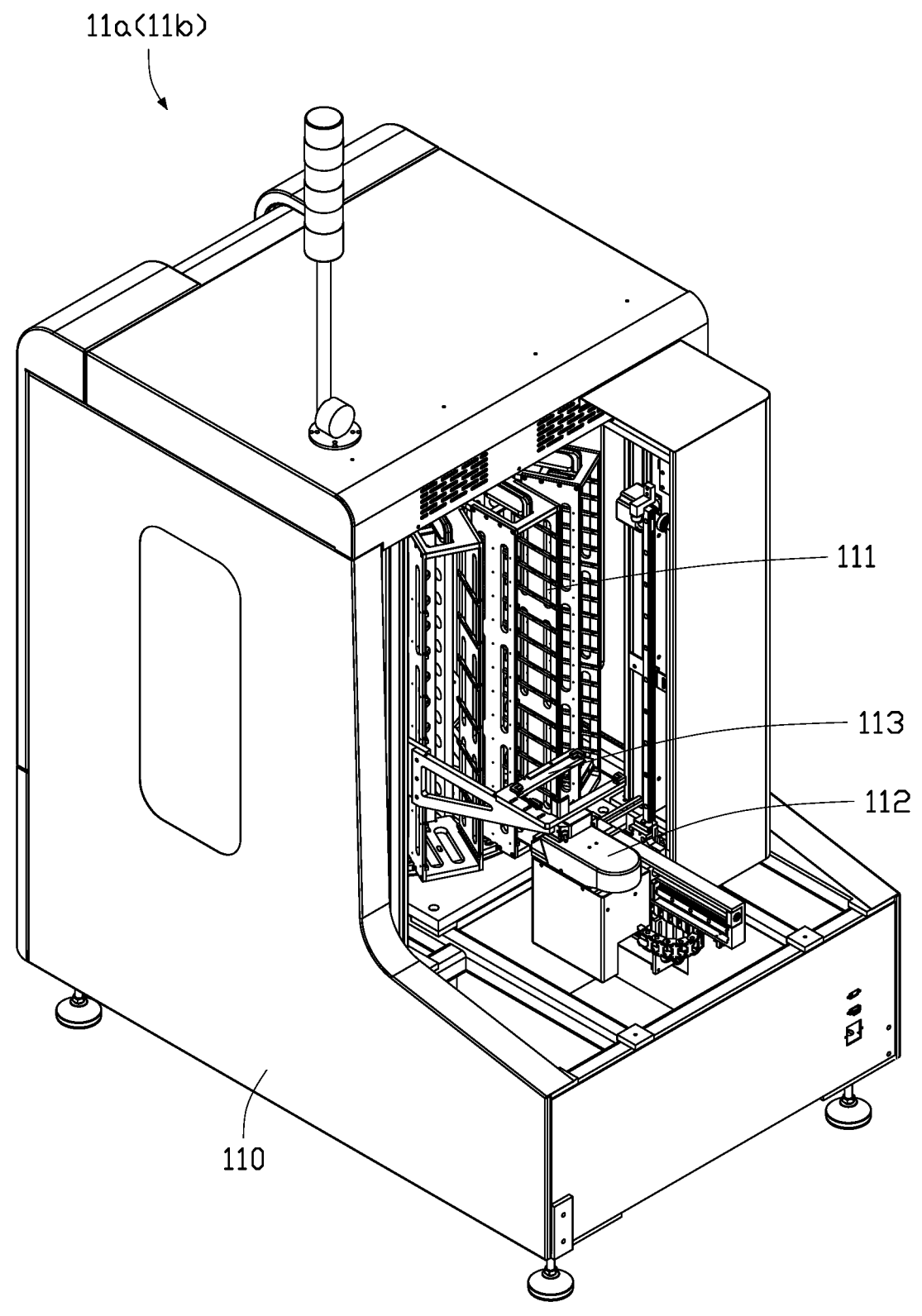
FIG. 4 is a perspective view of a consumable item storage device of the automated library preparation system of FIG. 1.
Figure 5:
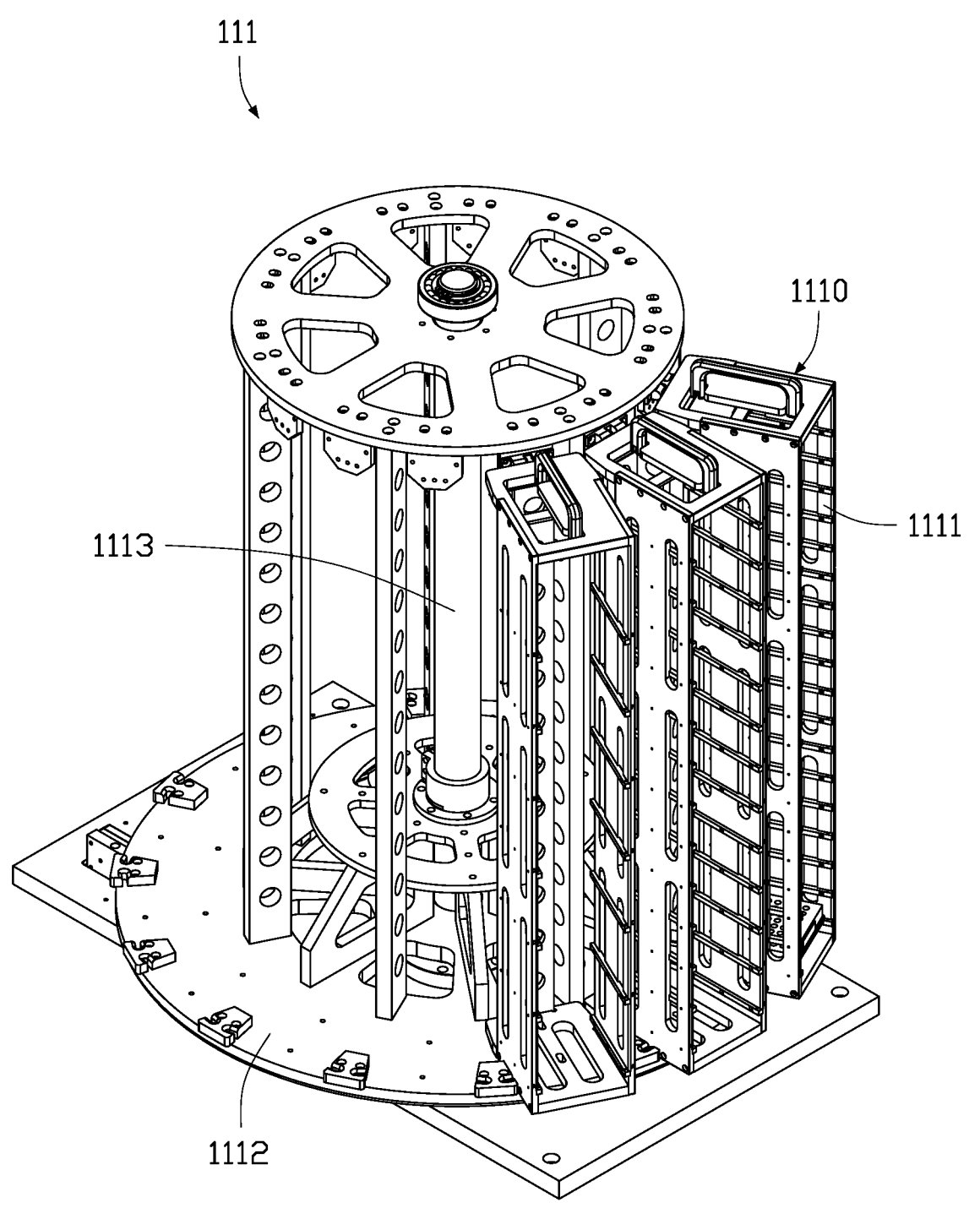
FIG. 5 is a perspective view of a storage rack of the consumable item storage device of FIG. 4.
Figure 6:
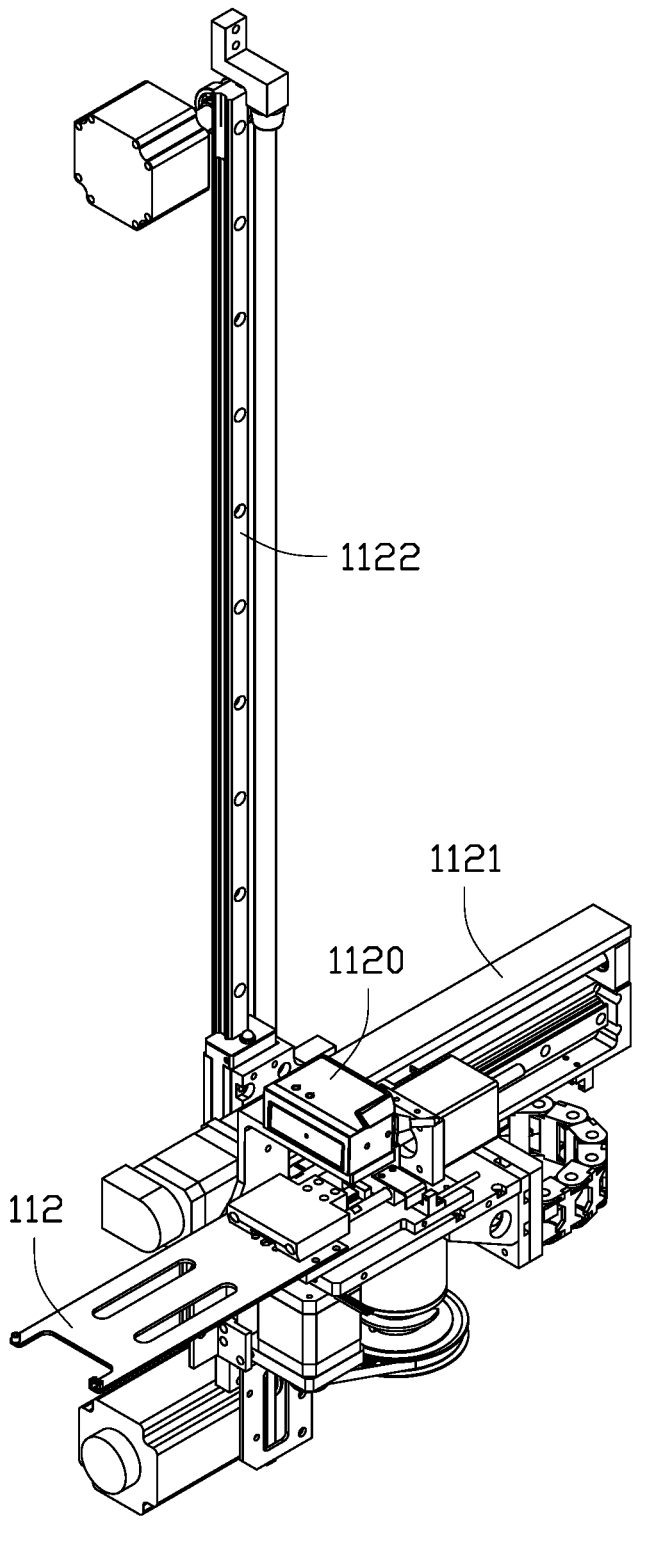
FIG. 6 is a perspective view of a discharging manipulator of the consumable item storage device of FIG. 4.

Referring to FIGS. 4 to 6, when the front consumable item storage device 11*a* is a normal temperature type consumable item storage device, it includes a housing 110, a storage rack 111, a discharging manipulator 112, and a discharging support plate 113. The storage rack 111, the discharging manipulator 112, and the discharging support plate 113 are disposed in the housing 110.

The storage rack 111 includes a plurality of stock bins 1110. Each stock bin 1110 is configured to store the consumable items 2. Each stock bin 1110 includes a plurality of layers of material racks 1111, which are stacked in a vertical direction. The storage rack 111 can further include a rotating plate 1112, and the plurality of stock bins 1110 are fixed on the rotating plate 1112. A support shaft 1113 is installed in the center of the rotating plate 1112, and the plurality of stock bins 1110 are distributed around the support shaft 1113. The rotating plate 1112 can rotate around the support shaft 1113, so that different stock bins 1110 on the rotating plate 1112 can be aligned with the discharging manipulator 112.

The discharging manipulator 112 can slide along a horizontal guide rail 1121 to adjust a distance between the discharging manipulator 112 and the stock bins 1110. The discharging manipulator 112 can also slide along a vertical guide rail 1122, so that the discharging manipulator 112 can be aligned with different material racks 1111 on one stock bin 1110, and the discharging manipulator 112 can clamp the consumable items 2 located in different material racks 1111. In this embodiment, the discharging manipulator 112 is provided with a first code scanner 1120, which is configured to scan a barcode on the consumable items 2 to obtain a serial number of the consumable items 2, so as to facilitate sample tracking management. The discharging manipulator 112 can also rotate within a certain range to align the discharging support plate 113 and transfer the clamped consumable items 2 to the discharging support plate 113. In this embodiment, the discharging manipulator 112 is a four-axis manipulator. Subsequently, the dispatching transfer module 30 will dispatch and transfer the consumable items on the discharging support plate 113 to different biochemical reaction devices 21 for automated library preparing.

Figure 7:
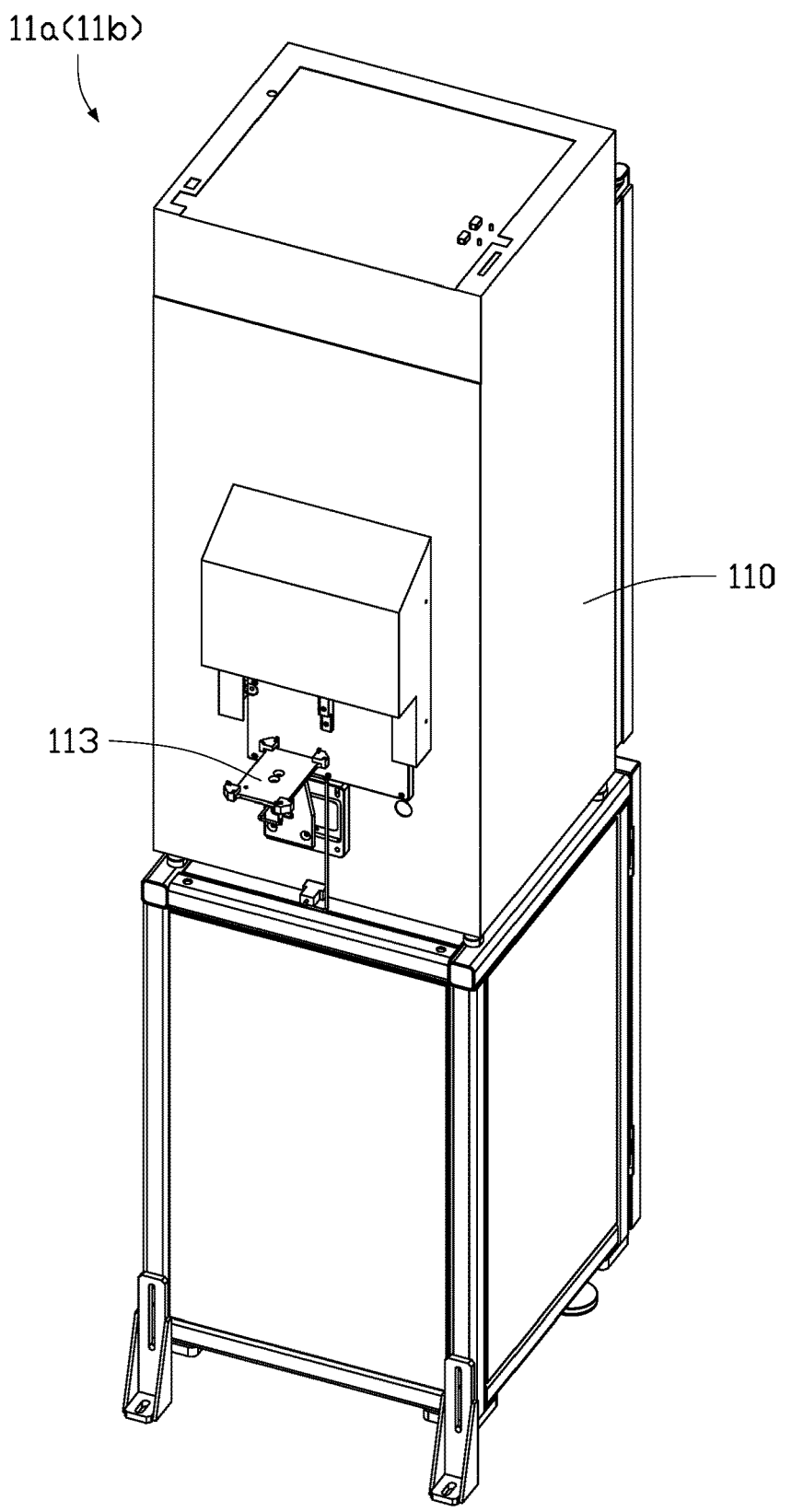
FIG. 7 is a perspective view of another consumable item storage device of the automated library preparation system of FIG. 1.

Referring to FIG. 7, when the front consumable item storage device 11*a* is a low-temperature type consumable item storage device, its structure is similar to that of the normal temperature type consumable item storage device. The difference is that the housing 110 of the low-temperature type consumable storage device is a closed chamber, which is used to provide a low-temperature storage environment. The storage rack 111 and the discharging manipulator 112 of the low-temperature type consumable item storage device are both housed in the closed chamber formed by the housing 110, and the discharging support plate 113 is arranged outside the housing 110.

The rear consumable item storage device 11*b* can also be provided with the normal temperature type consumable item storage device and/or the low temperature type consumable item storage device according to actual needs.

Figure 8:
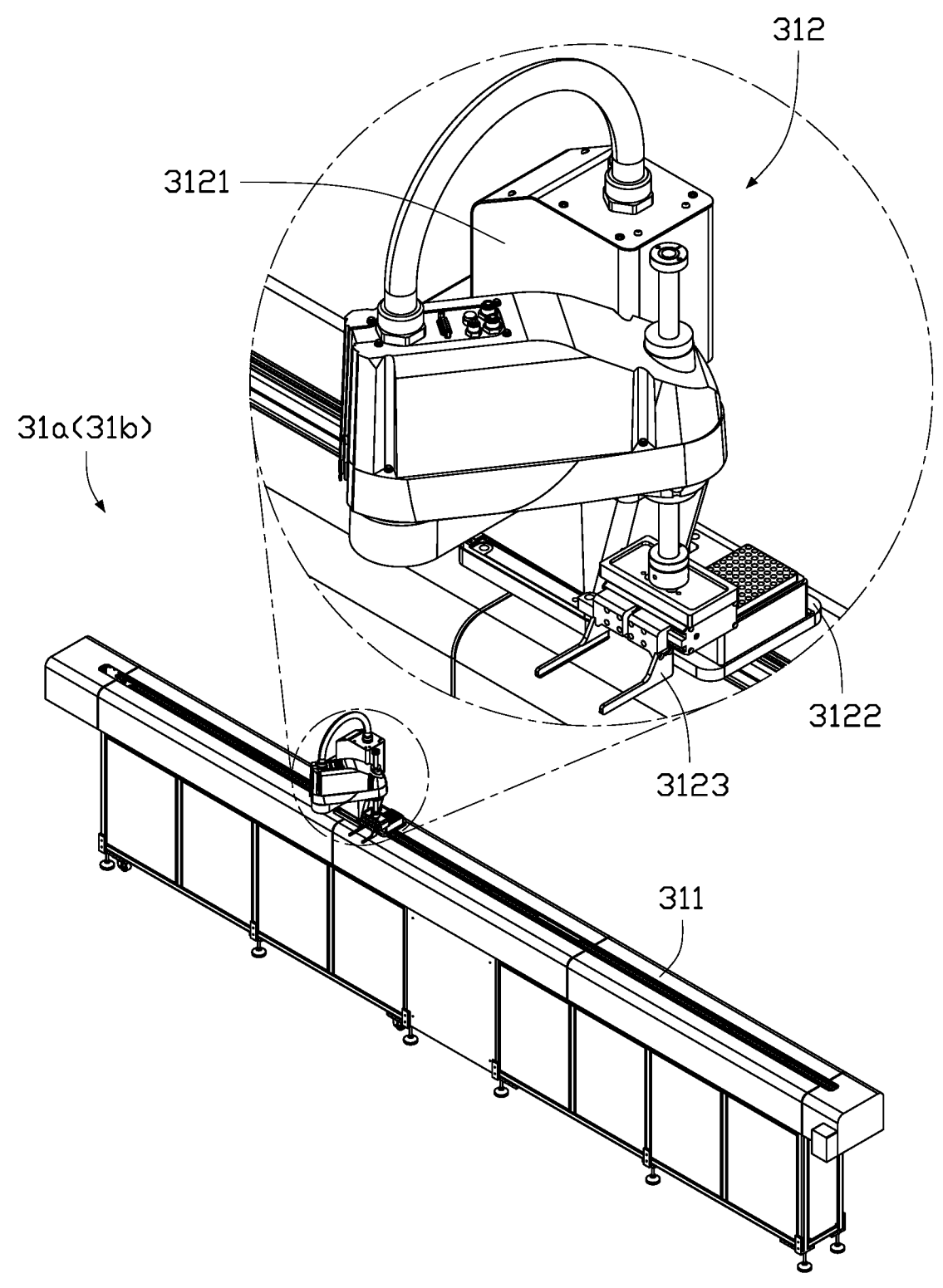
FIG. 8 is a perspective view of a dispatching transfer device of the automated library preparation system of FIG. 1.

As shown in FIG. 1, the dispatching transfer module 30 includes dispatching transfer devices located in the pre-processing area 100*a* and post-processing area 100*b* respectively. For the convenience of expression, the dispatching transfer device located in the pre-processing area 100*a* is defined as a front dispatching transfer device 31*a*, and the dispatching transfer device located in the post-processing area 100*b* is defined as a rear dispatching transfer device 31*b*. Referring to FIG. 8, each dispatching transfer device includes a slide rail 311 extending in the predetermined direction and a dispatching transfer assembly 312 slidably arranged on the slide rail 311. Each consumable item storage device is located on one side of the slide rail 311, while the plurality of biochemical reaction devices are located on the other side of the slide rail 311 and arranged in turn along an extending direction of the slide rail 311. The front dispatching transfer device 31*a* is configured to transfer the consumable items 2 to the plurality of front biochemical reaction devices 21*a* located in the pre-processing area 100*a* for reaction, and then the consumable items 2 are placed in the consumable item accommodation chamber 410 through the front automatic door 42 of the transfer window device 40 after the subprocess in the pre-processing area 100*a* is completed.

The rear dispatching transfer device 31*b* is configured to take away and transfer the consumable items placed in the consumable item accommodation chamber 410 to the plurality of rear biochemical reaction devices 21*b* located in the post-processing area 100*b* for reaction. The total thread of the slide rail 311 of the front dispatching transfer device 31*a* and the rear dispatching transfer device 31*b* is long, so that the entire sliding path of the two dispatching transfer assemblies 312 can cover all biochemical reaction devices.

The dispatching transfer assembly 312 includes a dispatching manipulator 3121, a consumable item buffer plate 3122 arranged at an end of the dispatching manipulator 3121, and a clamping jaw 3123 arranged at the other end of the dispatching manipulator 3121. The dispatching manipulator 3121 can slide along the slide rail 311 and can further rotate horizontally or vertically to adjust the position of the clamping jaw 3123. Therefore, the clamping jaw 3123 can first be aligned with the consumable item storage devices 11*a* and 11*b*, clamp the consumable items 2 on the discharging support plate 113, and place them on the consumable item buffer plate 3122. Then, the clamping jaw 3123 changes its position to align with the biochemical reaction device 21, clamps the consumable items 2 on the consumable item buffer plate 3122, and transfers them to the biochemical reaction device. In this embodiment, the dispatching manipulator 3121 is a horizontal multi-joint manipulator.

Different biochemical reaction devices have different structures according to the different sub-processes.

Figure 9:
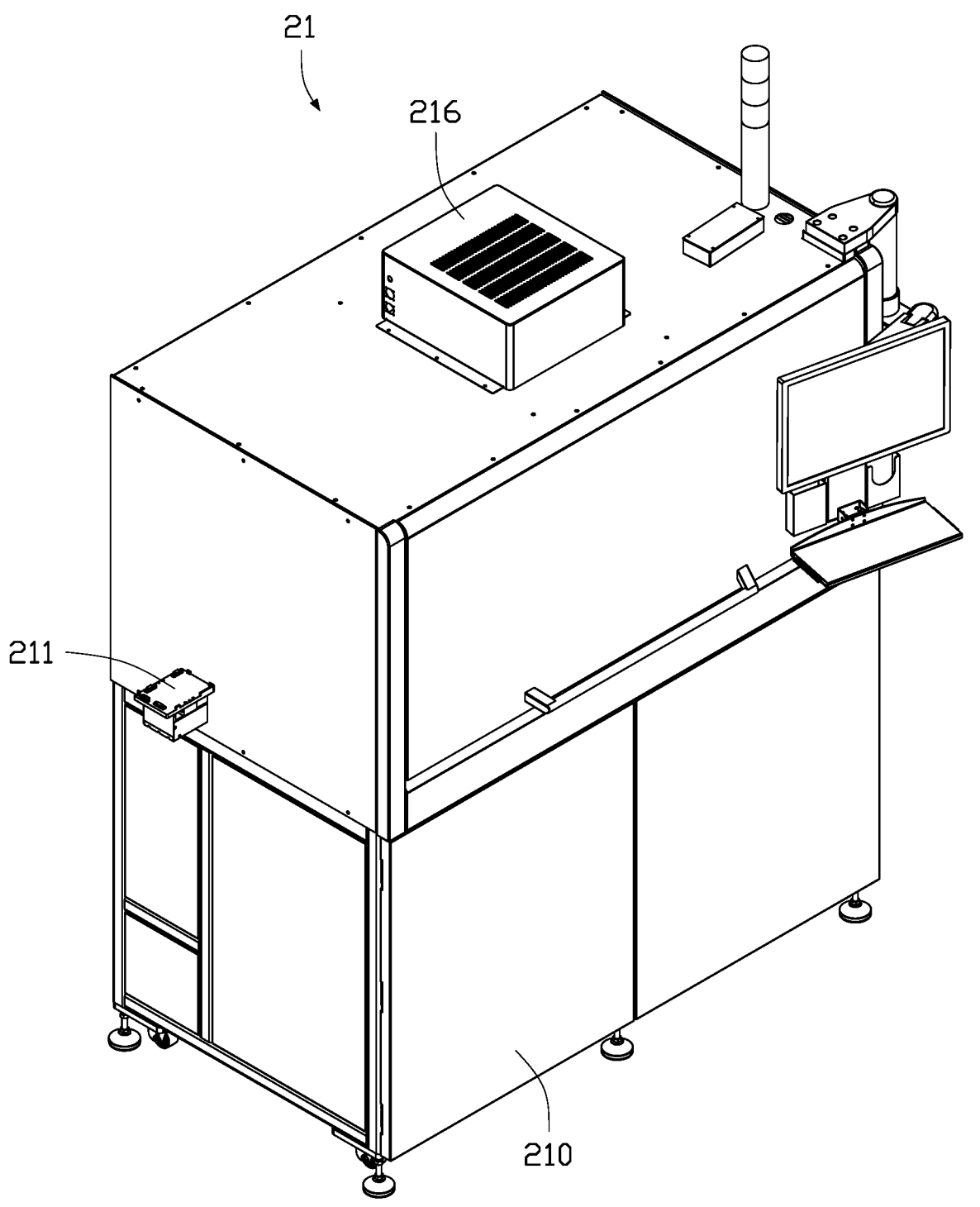
FIG. 9 is a perspective view of a biochemical reaction device of the automated library preparation system of FIG. 1.
Figure 10:
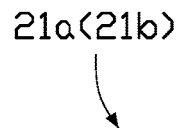
FIG. 10 is a perspective view of the biochemical reaction device of FIG. 9 without a laminar flow hood.

Referring to FIG. 9 and FIG. 10, the following describes an example of a structure of a biochemical reaction device which is configured for performing sub-processes of PCR amplification and purification. The biochemical reaction device includes a frame 210, an output and input bit 211, a pipetting unit 212, a temperature control unit 213, an amplification unit 214, a magnetic bead purification unit 215, and a vibrating unit 218. The output and input bit 211, the pipetting unit 212, the temperature control unit 213, the amplification unit 214, the magnetic bead purification unit 215, and the vibrating unit 218 are disposed on the frame 210. The dispatching transfer device is configured to transfer the consumable items containing samples output by the previous biochemical reaction device to the output and input bit 211 of the current biochemical reaction device, and further to clamp the consumable items 2 in the consumable item storage device and transfer them to the output and input bit 211. The pipetting unit 212 is configured to transfer various consumable items 2 placed on the output and input bit 211 to the corresponding working position. The vibrating unit 218 is configured to shake and mix the sample or reagent in the consumable item 2. The temperature control unit 213 is configured for heating or cooling the reagent in the consumable item 2 to provide a suitable temperature for the subsequent biochemical reaction. The amplification unit 214 is configured to amplify the sample in the consumable item 2. The magnetic bead purification unit 215 is configured to clean magnetic beads and purify the amplified nucleic acid molecules.

Figure 11:
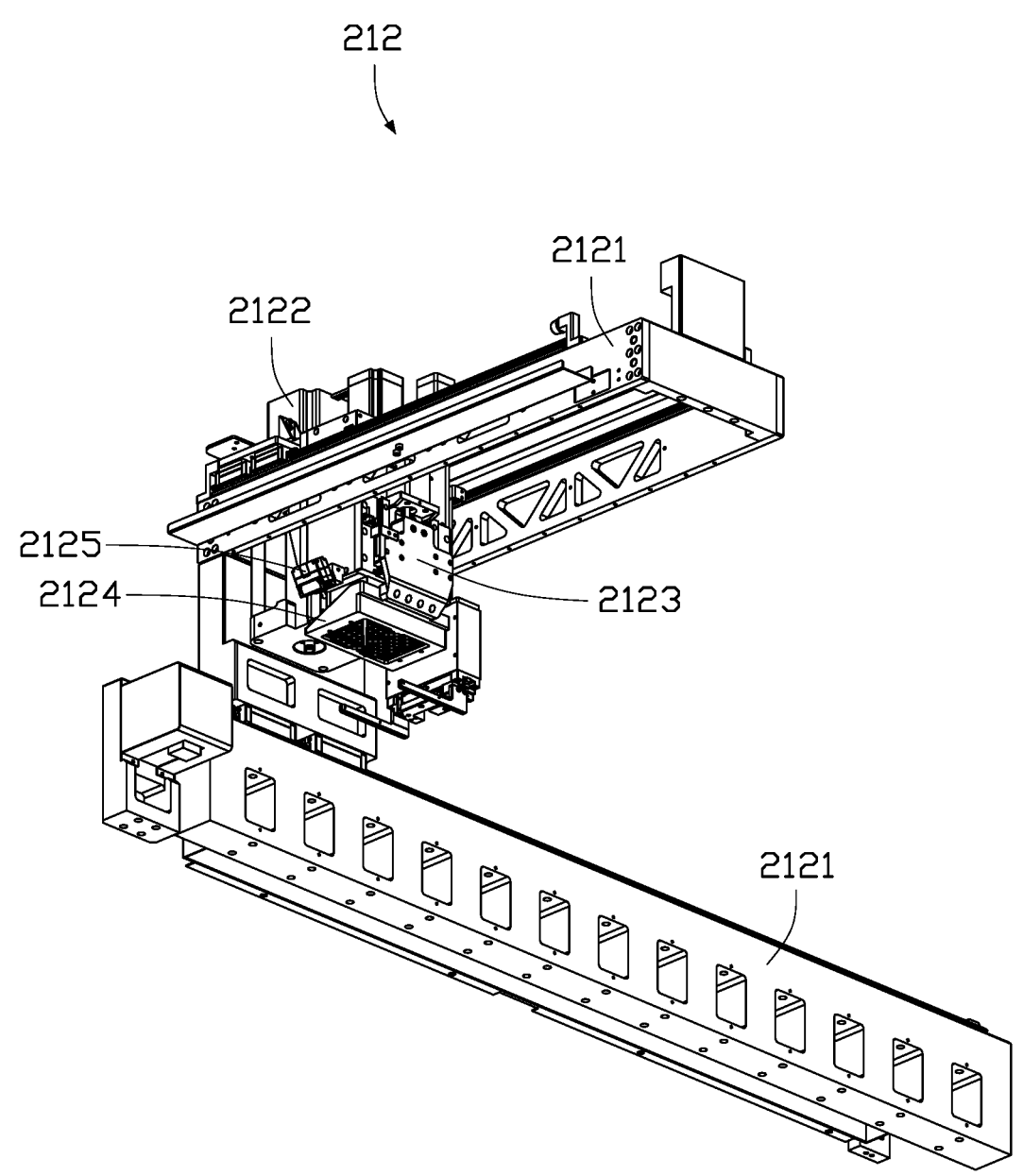
FIG. 11 is a perspective view of pipetting unit of the biochemical reaction device of FIG. 10.

Referring to FIG. 11, in this embodiment, the pipetting unit 212 includes a pipetting manipulator 2123, an automatic pipette 2124 connected to the pipetting manipulator 2123, and a tip placement location (not shown). The tip placement location is configured to place a tip frame with a tip. The pipetting manipulator 2123 can slide along two horizontal guide rails 2121 which are perpendicular to each other and can slide along the vertical guide rail 2122, so as to control the automatic pipette 2124 to move to the required position, thereby facilitating the automatic pipette 2124 to absorb and transfer liquid. In this embodiment, the automatic pipette 2124 is an automatic pipette with ninety-six channels. A second code scanner 2125 can be disposed on the pipetting unit 212. The second code scanner 2125 is configured to scan the barcode on the consumable item 2 to obtain the serial number of the consumable item 2, which is convenient for sample tracking management.

In this embodiment, the biochemical reaction device can also be further equipped with a laminar flow hood 216 on the frame. PCR amplification and post-purification reactions are carried out in the laminar flow hood 216, so as to further prevent cross-contamination between the sample and the environment.

Figure 12:
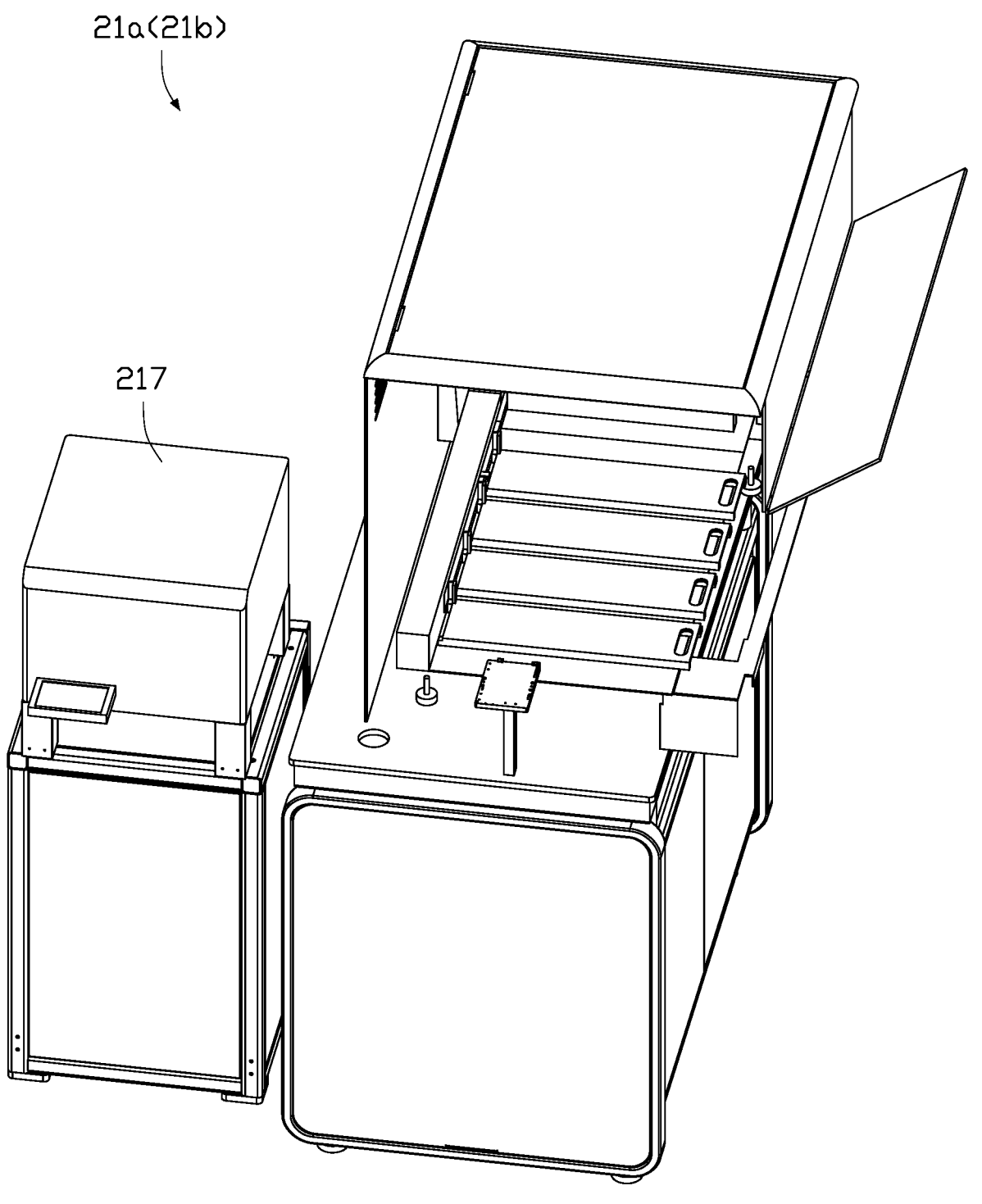
FIG. 12 is a perspective view of another biochemical reaction device of the automated library preparation system of FIG. 1.

Referring to FIG. 12, the following describes an example of a structure of a biochemical reaction device which is configured to perform the sub-process of quantitative. The biochemical reaction device also includes an output and input bit and a pipetting unit. When the dispatching transfer device transfers the consumable item 2 output by the previous biochemical reaction device and the consumable item 2 in the consumable item storage device to the output and input site of the biochemical reaction device, the pipetting unit transfers the various consumable items 2 placed on the output and input site to the corresponding working position. The biochemical reaction device further includes a microplate reader 217 which is configured to perform a quantitative analysis and a purity analysis of samples in the consumable item 2. In this embodiment, the automatic pipette of the pipetting unit is a variable spacing automatic pipette with eight channels. Of course, the microplate reader can be replaced by a fluorescence quantitative instrument.

Figure 14:
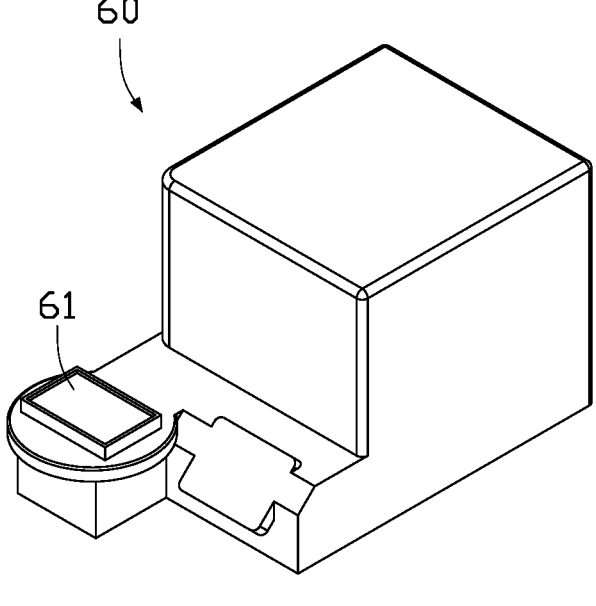
FIG. 14 is a perspective view of a film peeling device of the automated library preparation system of FIG. 1.

In this embodiment, as shown in FIG. 1, the automated library preparation system 1 further includes a film sealing device 50 and a film peeling device 60. After the consumable item 2 is taken out of the consumable item storage device by the dispatching transfer module 30, the dispatching transfer module 30 is further configured to place the consumable item 2 on a consumable item loading site 61 of the film peeling device 60. Referring to FIG. 14, the film peeling device 60 is configured to remove a packaging film on the consumable 2 by a physical manner. When the reaction is completed, the dispatching transfer module 30 is further configured to grab the consumable item 2 and place it on a consumable item loading site 51 of the film sealing device

Figure 13:
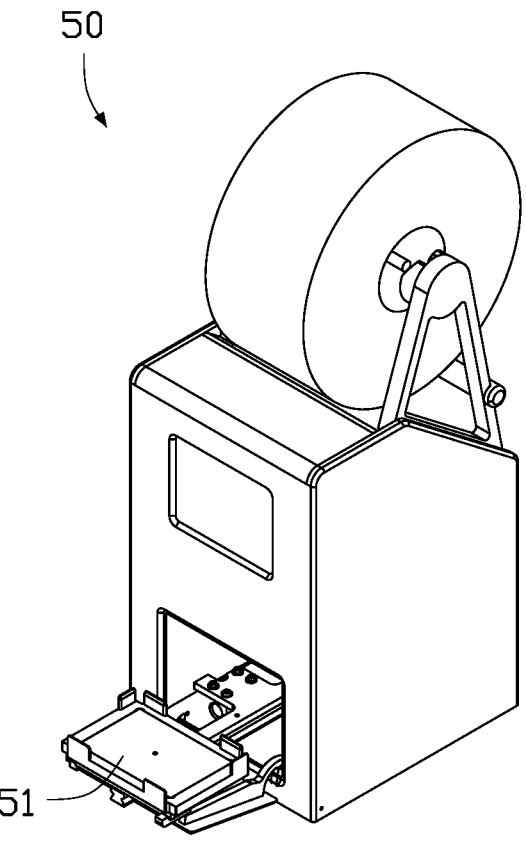
FIG. 13 is a perspective view of a film sealing device of automated library preparation system of FIG. 1.

50. Referring to FIG. 13, the film sealing device 50 is configured to apply a layer of packaging film on the consumable item 2 by hot melting, so as to prevent the sample in the consumable item 2 from evaporating and/or being contaminated by other reagents.

Figure 15:
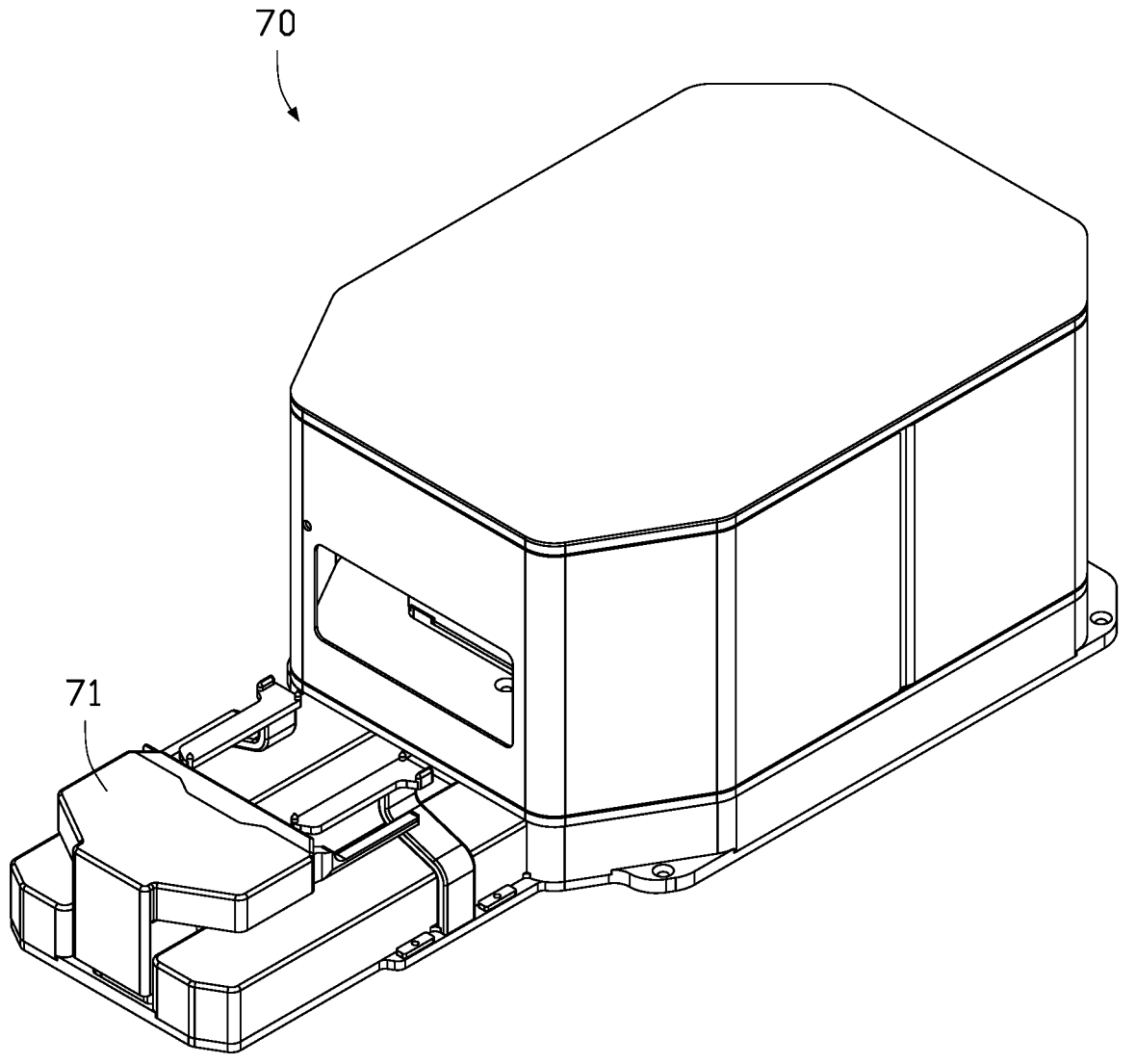
FIG. 15 is a perspective view of a centrifuge device of the automated library preparation system of FIG. 1.

The automated library preparation system 1 can further include a centrifuge device 70. The dispatching transfer module 30 is also configured to place the consumable item 2 on a consumable item loading site of the centrifuge device 70 before transferring the consumable item 2 to the biochemical reaction device. Referring to FIG. 15, the centrifuge device 70 is configured to centrifugally process liquid in the consumable item 2, so that the liquid of the consumable liquid accumulates at a bottom of the consumable item 2.

Referring to FIG. 1 and FIG. 16, in this embodiment, the automated library preparation system 1 further includes human-machine interface module 80. The human-machine interface module 80 includes two human-machine interface devices, which are respectively located in the pre-processing area 100a and the post-processing area 100b. For the convenience of expression, the human-machine interface device located in the pre-processing area 100a is defined as a front human-machine interface device 81a, and the human-machine interface device located in the post-processing area 100b is defined as a rear human-machine interface device 81b. The front human-machine interface device 81a and the rear human-machine interface device 81b are respectively equipped with a supporting platform 810 and a display device 815 located on the supporting platform 810. The display device 815 is used for an operator to monitor the processes of biochemical reaction in the pre-processing area 100a and the post-processing area 100b, so that the operator can timely intervene in case of any abnormality. When all biochemical subprocesses are completed, the dispatching transfer device is further configured to transfer the finally obtained gene sequencing sample to the rear human-machine interface device 81b, then it will be taken away by the operator.

Figure 17:
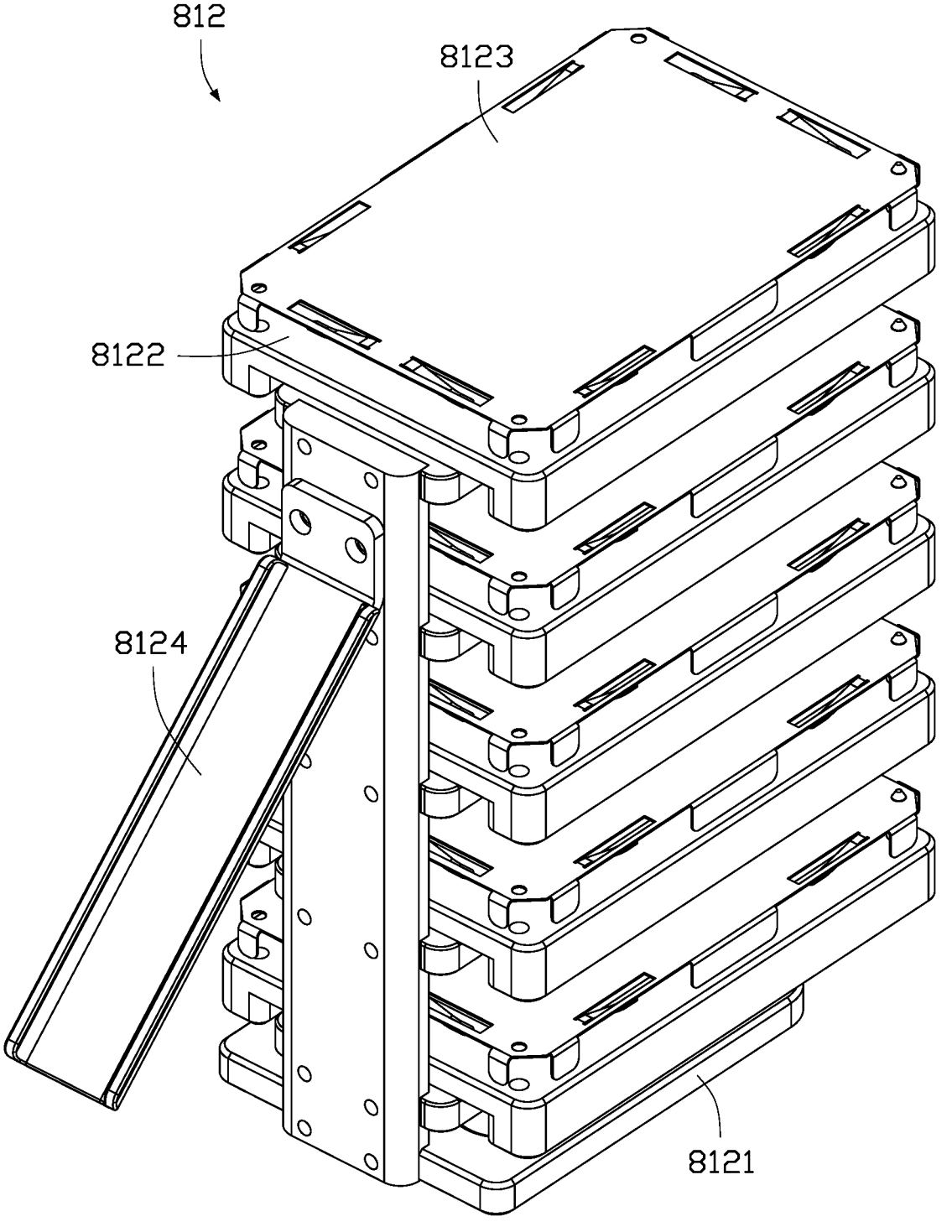
FIG. 17 is a perspective view of a consumable item stack bit of the human-machine interface module of FIG. 16.

The front human-machine interface device 81a and the rear human-machine interface device 81b further include an output and input bit 811, a rubber pad stack bit 812, a third code scanner 813, and a consumable item conveying unit 814 which are located on the supporting platform 810. The third code scanner 813 is located above the output and input bit 811 and is configured to scan the barcode on the consumable item 2 which is transferred to the output and input bit 811 to obtain the serial number of the consumable item 2 for sample tracking management. Referring to FIG. 17, a plurality of layers of rubber pad support 8121 is disposed on the rubber pad stack bit 812. A plurality layers of rubber pad supports 8121 are disposed on the rubber pad stack bit 812, each of the rubber pad supports 8121 is provided with a rubber pad positioning plate 8122 and a silicone pad 8123 located on the rubber pad positioning plate 8122, and the silicone pad 8123 is configured to seal the consumable item 2. The silicone pad 8123 needs to be disinfected after each use, so that it can be reused next time. The arrangement of the supporting platform 810 facilitates the operators to manually wipe and disinfect the silicone pad 8123. A handle 8124 can be disposed on the rubber pad support 8121 for the convenience of the operator. The consumable conveying unit 814 can be configured to place the final gene sequencing sample.

In conclusion, the automated sequencing system provided by the embodiments of the present disclosure realizes the one-stop automated sample preparation process. After the sample is input, the library sample for gene sequencing can be output, human intervention is reduced, and each module can conduct parallel pipeline operations, the throughput and efficiency of library construction are improved. The whole process is carried out in a sealed chamber, environmental pollution and cross-contamination between samples are avoided, the quality of gene sequencing samples is improved, and the results are more accurate and reliable.

The above-mentioned embodiments are only used to illustrate but not to limit the technical scheme of the present disclosure, and the present disclosure is described in details only according to the preferable embodiments. Those skilled in the art should understand that they can make the modifications and equivalent replacements according to the technical scheme of the present disclosure without departing from the spirit and scope of technical scheme of the present disclosure, which should be included in the scope of the appended claims of the present disclosure.

What is claimed is:

1. An automated library preparation system, comprising:
a plurality of consumable item storage devices configured for storing a consumable item;
at least two dispatching transfer devices movable in a first direction; and
a plurality of biochemical reaction devices which are spaced apart in the first direction, each of the plurality of biochemical reaction devices being configured to perform one subprocess of sample preparation for gene sequencing, wherein each of the at least two dispatching transfer devices is configured to grab a consumable item stored in a corresponding consumable item storage device of the plurality of consumable item storage devices, each of the at least two dispatching transfer devices is further configured to transfer a consumable item to the plurality of biochemical reaction devices as the at least two dispatching transfer devices sliding in the first direction;
each of the plurality of consumable item storage devices comprises a storage rack for storing a consumable item, a discharging support plate, a discharging manipulator, a horizontal guide rail, and a vertical guide rail, the discharging manipulator is slidably disposed on the horizontal guide rail and the vertical guide rail and is configured to clamp a storage item in the storage rack and transfer the clamped consumable item to the discharging support plate;
each of the at least two dispatching transfer devices comprises a dispatching transfer assembly, the dispatching transfer assembly comprises a dispatching manipulator, a consumable item buffer plate arranged at a first end of the dispatching manipulator, and a clamping jaw arranged at a second end of dispatching manipulator, and the dispatching manipulator is configured to drive the clamping jaw to clamp a consumable item on the discharging support plate and transfer clamped consumable item to the consumable buffer plate.

2. The automated library preparation system of claim 1, wherein the automated library preparation system comprises at least two processing areas which are separated from each other, each of the at least two processing areas encloses a closed chamber, the at least two processing areas are arranged in the first direction, at least one of the plurality of biochemical reaction devices is located in each of the at least two processing areas.

3. The automated library preparation system of claim 2, wherein a transfer window device is arranged between two adjacent processing areas of the at least two processing areas, the transfer window is configured to maintain separation between the two adjacent processing areas when one of the at least two dispatching transfer devices transfers a consumable item from one of the two adjacent processing areas of the plurality of processing areas to the other of the two adjacent processing areas of the plurality of processing areas, the transfer window device comprises a front automatic door and a rear automatic door, when one of the at least two dispatching transfer devices transfers a consumable item from one of the two adjacent processing areas of the plurality of processing areas to the other of the two adjacent processing areas of the plurality of processing areas, one of the front automatic door and the rear automatic door is opened, and the other of the front automatic door and the rear automatic door is closed to maintain separation between the two adjacent processing areas.

4. The automated library preparation system of claim 3, wherein the transfer window device further comprises a separating block the front automatic door is disposed on a first side of the separating block, the rear automatic door is disposed on a second side of the separating block which is opposite to the first side of the separating block, the separating block defines a consumable item accommodation chamber, the consumable item accommodation chamber is configured to accommodate a consumable item transferred from one of the two adjacent processing areas of the plurality of processing areas, the front automatic door and the rear automatic door are configured to close opposite sides of the consumable item accommodation chamber when the front automatic door and the rear automatic door are closed.

5. The automated library preparation system of claim 2, wherein the plurality of consumable item storage devices are respectively located in the at least two processing areas, one of the plurality of consumable item storage devices in a corresponding processing area of the at least two processing areas is configured to provide a consumable item for a corresponding biochemical reaction device of the plurality of the biochemical reaction devices in the corresponding processing area.

6. The automated library preparation system of claim 5, wherein corresponding consumable item storage devices of the plurality of consumable item storage devices in one of the at least two processing areas comprises a normal temperature type consumable item storage device and a low-temperature type consumable item storage device, the normal temperature type consumable item storage device is configured to provide a room temperature storage environment for storing a consumable item, the low-temperature type consumable item storage device is configured to provide a low-temperature storage environment for storing a consumable item.

7. The automated library preparation system of claim 5, wherein the at least two dispatching transfer devices are respectively disposed in each of the two processing areas, each of the at least two dispatching transfer devices comprises a slide rail extending in the first direction, the dispatching transfer assembly is slidably arranged on the slide rail.

8. The automated library preparation system of claim 1, further comprising a film sealing device and a film peeling device, the film sealing device being configured to apply a packaging film on a consumable item, the film peeling device being configured to remove the packaging film on a consumable item.

9. The automated library preparation system of claim 1, further comprising a centrifuge device, the centrifuge device being configured to centrifugally process liquid in a consumable item.

\* \* \* \* \*